US011651213B2

(12) United States Patent
Liu et al.

(10) Patent No.: US 11,651,213 B2
(45) Date of Patent: May 16, 2023

(54) METHOD OF PREDICTING CHROMATOGRAPHIC ELUTION ORDER OF COMPOUNDS

(71) Applicants: PUKYONG NATIONAL UNIVERSITY INDUSTRY-UNIVERSITY COOPERATION FOUNDATION, Busan (KR); Medical University of Gdańsk, Gdańsk (PL)

(72) Inventors: Jay Liu, Busan (KR); Petar Zuvela, Singapore (SG); Tomasz Bączek, Gdańsk (PL); Alham Alipuly, Busan (KR)

(73) Assignees: Pukyong National University Industry-University Cooperation Foundation, Busan (KR); Medical University of Gdansk, Gdansk (PL)

( * ) Notice: Subject to any disclaimer, the term of this patent is extended or adjusted under 35 U.S.C. 154(b) by 617 days.

(21) Appl. No.: 16/740,243

(22) Filed: Jan. 10, 2020

(65) Prior Publication Data

US 2020/0394513 A1 Dec. 17, 2020

(30) Foreign Application Priority Data

Jun. 13, 2019 (KR) .......................... 10-2019-0069924

(51) Int. Cl.
*G06N 3/08* (2023.01)
*G06N 3/04* (2023.01)
(Continued)

(52) U.S. Cl.
CPC ................. *G06N 3/08* (2013.01); *G06N 3/04* (2013.01); *G16C 20/30* (2019.02); *G16C 20/70* (2019.02)

(58) Field of Classification Search
CPC ........ G01N 30/8693; G06N 3/02; G06N 3/04; G06N 3/08; G16C 20/30; G16C 20/70
See application file for complete search history.

(56) References Cited

U.S. PATENT DOCUMENTS

| 5,958,784 A | 9/1999 | Benner |
| 2010/0161530 A1 | 6/2010 | Petritis et al. |

OTHER PUBLICATIONS

Patricia Payares, Prediction of the gas chromatographic relative retention times of flavonoids from molecular structure., Journal of Chromalography A. 771 ( 1997) 213-219 (Year: 1997).*

(Continued)

*Primary Examiner* — Yoshihisa Ishizuka
(74) *Attorney, Agent, or Firm* — Knobbe Martens Olson & Bear LLP

(57) ABSTRACT

Disclosed is a method for predicting an elution order of compounds in a mixture. The method includes (a) building a quantitative structure-retention relationship (QSRR) model and (b) predicting a chromatographic elution order of the compounds in the mixture on the basis of the QSRR model using mathematical programming. The mathematical programming is a non-linear programming technique in which a predicted elution order of the compounds is used as a constraint or a multi-objective optimization (MOO) in which a retention time prediction error and an elution order prediction error are used as objective functions. With the use of the method of the present disclosure, it is possible to optimize separation of complex mixtures in reversed-phase chromatography by enabling identification of accurate positions of individual compounds that provides higher certainty in identifying a given compound, e.g., during an "omics" analysis (proteomics, metabolomics, etc.).

7 Claims, 18 Drawing Sheets

(51) Int. Cl.
    *G16C 20/30*    (2019.01)
    *G16C 20/70*    (2019.01)

(56) References Cited

OTHER PUBLICATIONS

Amos et al., "Molecular modeling and prediction accuracy in Quantitative Structure-Retention Relationship calculations for chromatography," *Trends in Analytical Chemistry*, 105 (2018), 352-359.
Héberger, "Quantitative structure-(chromatographic) retention relationships," *Journal of Chromatography A*, 1158, (2007), 273-305.
Kaliszan, "QSSR: Quantitative Structure-(Chromatographic) Retention Relationships," *Chem. Rev.* 2007, 107, 3212-3246.

* cited by examiner

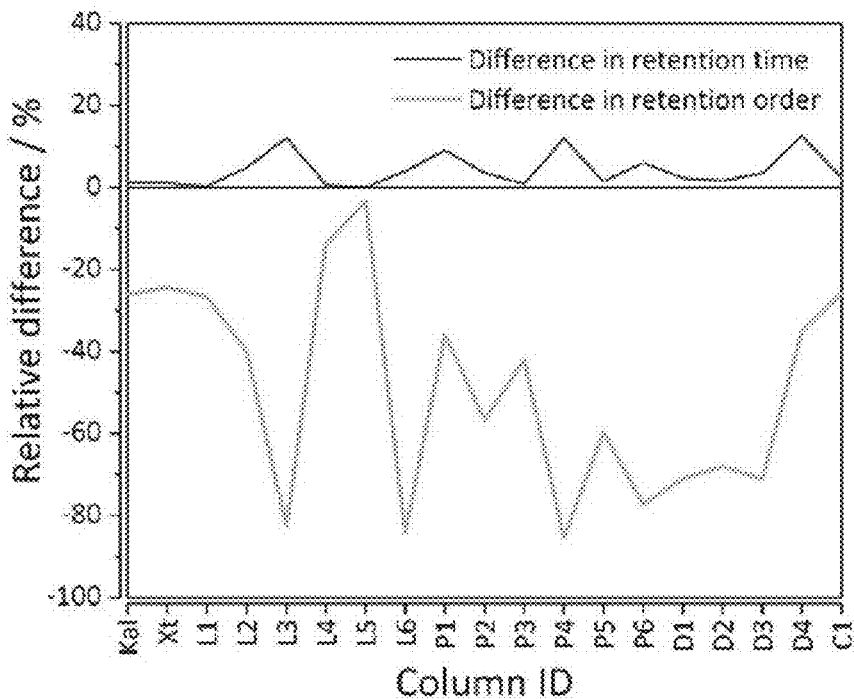

Legend:

Kal - CS1, Supelcosil LC ($t_G$ = 10 min, $T$ = 35°C)
Xt - CS2, Xterra ($t_G$ = 20 min, $T$ = 40 °C)
L1 - CS2, Licrospher ($t_G$ = 20 min, $T$ = 40 °C);
L2 - ($t_G$ = 60 min, $T$ = 40 °C); L3 - ($t_G$ = 120 min, $T$ = 40 °C);
L4 - ($t_G$ = 20 min, $T$ = 60 °C); L5 - ($t_G$ = 20 min, $T$ = 80 °C)
P1 - CS2, PRP ($t_G$ = 20 min, $T$ = 40 °C)
P2 - ($t_G$ = 60 min, $T$ = 40 °C); P3 - ($t_G$ = 20 min, $T$ = 60 °C)
P4 - ($t_G$ = 60 min, $T$ = 60 °C); P5 - ($t_G$ = 20 min, $T$ = 80 °C)
P6 - ($t_G$ = 60 min, $T$ = 80 °C)
D1 - CS2, RP-Amide C-16 ($t_G$ = 20 min, $T$ = 40 °C)
D2 - ($t_G$ = 20 min, $T$ = 60 °C); D3 - ($t_G$ = 20 min, $T$ = 80 °C)
L6 - CS2, Licrospher CN ($t_G$ = 20 min, $T$ = 40 °C)
D4 - CS2, HS F5-3 ($t_G$ = 20 min, $T$ = 40 °C)
C1 - CS2, Chromolith ($t_G$ = 20 min, $T$ = 40 °C)

FIG. 2C

METHOD OF PREDICTING CHROMATOGRAPHIC ELUTION ORDER OF COMPOUNDS

CROSS REFERENCE TO RELATED APPLICATION

The present application claims priority to Korean Patent Application No. 10-2019-0069924, filed Jun. 13, 2019, the entire contents of which is incorporated herein for all purposes by this reference.

BACKGROUND

1. Technical Field

The present disclosure relates to a method of predicting an order in which compounds in a mixture are eluted and, more particularly, to a method of accurately predicting elution order of compounds in a mixture on the basis of quantitative structure-retention relationships (QSRR) by using mathematical programming.

2. Description of Related Technology

QSRR-based prediction of retention time of each compound in a mixture is one of the most widely used powerful tools for development of chromatographic separation methods. While many studies and inventions have explained several advantages of prediction of retention time of each compound in a mixture to be analyzed with the use of a stationary phase in a chromatographic column, only few studies on prediction of elution order have been reported. In general, a QSRR model is considered as a highly accurate prediction method to theoretically estimate an order of eluted compounds in comparison to an order observed experimentally. However, QSRR models are applicable to only simple mixtures (i.e., simple mixtures of known composition of compounds).

However, the QSRR models are not so well applicable to reversed-phase liquid chromatography (RP-LC), which accounts for more than 90% of separation of complex mixtures (pharmaceuticals, proteins, etc.) because the RP-LC mechanism, although well described, is complex and is not yet fully understood. Thus, although QSRR models can predict retention time with a reasonable error for some cases, they often result in a poor prediction accuracy when it comes to cases where an elution order of hundreds or thousands of very close or overlapping peaks is predicted. Moreover, no research literature has presented an approach to solve problems with complex chromatography such as RP-LC.

SUMMARY

The present disclosure has been made to solve the problems occurring in the related arts, and an objective of the present disclosure is to provide a method of predicting elution order of compounds in a mixture, thereby optimizing separation of a complex mixture such as pharmaceuticals, peptides or proteins through reversed-phase liquid chromatography.

In order to accomplish the above objective, the present disclosure provides a method of predicting chromatographic elution order of compounds in a mixture, the method including: (a) building a model of quantitative structure-retention relationships; and (b) predicting the chromatographic elution order of the compounds in the mixture on the basis of the QSRR model by using mathematical programming, wherein the mathematical programming is (i) a non-linear programming technique in which the predicted elution order is used as a constraint or (ii) a multi-objective optimization (MOO) technique in which the both (retention time and elution order) prediction errors are used as objective functions.

In addition, the QSRR model obtained through (a) modeling may be a linear model represented by the following formula:

$$t_{R,j} = a_1 x_{j,1} + a_2 x_{j,2} + \ldots + a_n x_{j,n}$$

wherein $t_{R,j}$ are retention times of respective compounds j arranged in ascending order, $x_{j,i}$ (i=1, ..., n) are molecular descriptors of respective compounds j, and $a_i$ (i=1, ..., n) are regression coefficients.

In addition, the QSRR relation model obtained through the (a) modeling may be a non-linear model obtained by using a non-linear regression equation, such as e.g., an artificial neural network (ANN).

In addition, in (b) prediction, the chromatographic elution order of the compounds in the mixture may be predicted under constraints of an inequality (Formula II) disclosed below by using non-linear programming (Formula I) described below.

$$\min_{\bar{a}} \left\{ \sum_{j=1}^{m}(t_{R,j} - a_1 x_{j,1} - a_2 x_{j,2} - a_3 x_{j,3})^2 + \sum_{j=1}^{m} \alpha_j \right\} \quad (I)$$

$$a_1(x_{j,1} - x_{j+1,1}) + a_2(x_{j,2} - x_{j+1,2}) + a_3(x_{j,3} - x_{j+1,3}) - \alpha_j \leq 0 \quad (II)$$

In the inequality, $a_j$ is a positive relaxation parameter, and $\bar{a}$ is a determinant vector set consisting of a1, a2, a3, and $a_j$ (j=1, 2, ..., m−1)).

In (b) prediction, the chromatic elution order of the compounds in the mixture may be predicted by performing a multi-objective optimization based on objective functions that respectively represent a retention time prediction error represented by Formula III and an elution order prediction error represented by Formula IV.

$$\% \; RMSE(t_R) = \sqrt{\sum \left(\frac{t_R - \hat{t}_R}{t_R}\right)^2 / m} \times 100 \quad (III)$$

In Formula III, $t_R$ and $\hat{t}_R$ represent retention time measured through an analytical experiment and a retention time predicted by the model, respectively, and m represents the number of mixtures measured for each column.

$$\% \; RMSE \; (\text{order}) = \sqrt{\sum \left(\frac{\text{order}_{pred.} - \text{order}_{obs.}}{\text{order}_{obs.}}\right)^2 / m} \times 100 \quad (IV)$$

Herein, in Formula IV, $\text{order}_{obs.}$ and $\text{order}_{pred.}$ represent elution order determined through an analytical experiment and elution order determined from predicted retention time, respectively.

In (b) prediction, multi-objective optimization is carried out and a Pareto-optimal solution is selected by performing the steps described below:

(b-1) selecting a knee point that is an optimal compromise between the retention time prediction error and the elution order prediction error from a Pareto front consisting of Pareto solutions;

(b-2) moving to the next Pareto solution that reduces the elution order prediction error;

(b-3) verifying the solution using an applicability domain; and (b-4) repeating (b-1) and (b-2) until an increase in retention time prediction error reaches predetermined threshold or an outlier in the applicability domain exceeds a second predetermined threshold.

The present disclosure relates to a method of accurately predicting elution order of compounds in a mixture using non-linear programming or multi-objective optimization (MOO) by using predicted elution order of compounds as a constraint or using a retention time prediction error and an elution order prediction error as objective functions. According to the present disclosure, separation of complex mixtures through chromatography, especially reversed-phase chromatography, can be optimized by enabling accurate identification of positions of compounds, which provides greater certainty in identifying a given compound.

The present disclosure relates to a method of accurately predicting elution order of compounds in a mixture through mathematical programming (non-linear programming) or multi-objective optimization (MOO) by using predicted elution order of compounds as a constraint or using a retention time error and an elution order error as objective functions on the basis of a quantitative structure-retention relationship (QSRR). According to the present disclosure, separation of complex mixtures through chromatography, especially reversed-phase chromatography, can be optimized by enabling accurate identification of positions of compounds, which provides greater certainty in identifying a given compound.

BRIEF DESCRIPTION OF THE DRAWINGS

FIGS. 2A, 2B and 2C illustrate the results of a multi-objective optimization technique in which a retention time prediction error and an elution order prediction error are used as objective functions and more particularly illustrates the results of comparison between %RMSE values of MLR and MLR-MOO for each column in two examples wherein FIG. 2A is retention time, FIG. 2B is elution order, and FIG. 2C is %RMSE value difference between an MLR model and an MLR-MOO model;

FIGS. 3A, 3B, 3C, 3D, 3E and 3F illustrate the results of a multi-objective optimization technique in which a retention time prediction error and an elution order prediction error are used as objective functions and more particularly illustrate the performance of the present disclosure for a linear QSRR (MLR) wherein FIG. 3A is retention time, FIG. 3B is elution order, and FIG. 3C is an applicability domain in Example 1 (CS1); and FIG. 3D is retention time, FIG. 3E is elution order, and FIG. 3F is applicability domain in Example 2 (CS2); and FIGS. 4A, 4B and 4C illustrate the results of non-linear programming using predicted elution order as a constraint and, more particuarly, illustrate the results of comparison between %RMSE values of MLR and NLP (nonlinear programming) for each column in two examples in which FIG. 4A is retention time, FIG. 4B is elution order, and FIG. 4C is %RMSE value difference between an MLR model and an MLR-MOO model;

FIGS. 5A, 5B and 5C illustrate the results of non-linear programming using the predicted elution order as a constraint and more particularly shows the performance of the present disclosure (Example 2 (CS2)) for a linear QSRR (MLR) in which FIG. 5A is retention time prediction, FIG. 5B is elution order prediction, and FIG. 5C is applicability domain;

FIGS. 6A and 6B are graphs showing an MLR-MOO Pareto front wherein FIG. 6A is Example 1 (CS1) and FIG. 6B is Example 2 (CS2).

DETAILED DESCRIPTION

Figure 1:
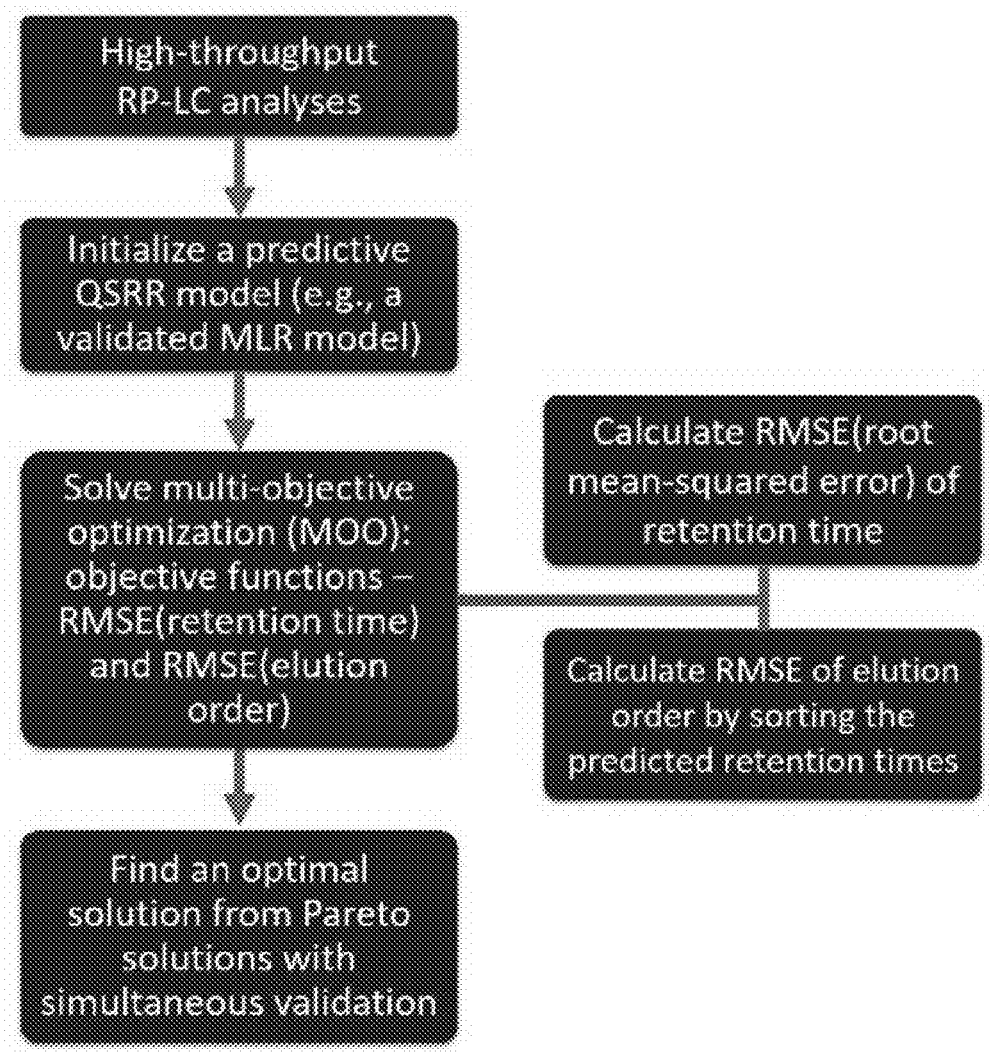
FIG. 1 is a conceptual explanatory diagram illustrating a method of predicting chromatographic elution order of compounds by using a multi-objective optimization (MOO) technique.

In describing embodiments of the present disclosure, well-known functions or constructions will not be described in detail when they may obscure the gist of the present invention.

Embodiments in accordance with the concept of the present invention can undergo various changes to have various forms, and only some specific embodiments are illustrated in the drawings and described in detail in the present disclosure. While specific embodiments of the present disclosure are described herein below, they are only for illustrative purposes and should not be construed to limit the scope of the present disclosure. The present disclosure should be construed to cover not only the specific embodiments but also cover all modifications, equivalents, and substitutions that fall within the concept and technical spirit of the present disclosure.

The terminologies used herein are for the purpose of describing particular embodiments only and is not intended to limit the scope of the present disclosure. As used herein, the singular forms "a", "an", and "the" are intended to include the plural forms as well unless the context clearly indicates otherwise. It will be further understood that the terms "comprises", "includes", or "has" when used in the present disclosure specify the presence of stated features, regions, integers, steps, operations, elements and/or components, but do not preclude the presence or addition of one or more other features, regions, integers, steps, operations, elements, components and/or combinations thereof.

The present disclosure describes a method for solving problems with prediction of elution order through QSRR-based mathematical programming in which a retention time error and an elution order error are defined as parts of an objective function. For a linear model, the gist of the present disclosure is a general QSRR model defined by Formula 1.

$$t_{R,j} = a_1 x_{j,1} + a_2 x_{j,2} + \ldots + a_n x_{j,n} \quad (1)$$

In Formula 1, $t_{R,j}$ are retention times of compounds j arranged in ascending order, $x_{j,i}$ (i=1, ..., n) are molecular descriptors of compounds j, and $a_i$ (i 1, ..., n) are regression coefficients, in which $t_{R,j}$ and $x_{j,i}$ are set such that their mean is adjusted to 0. The $a_i$ can be obtained through multiple linear regression (MLR). When the QSRR is non-linear, a non-linear modeling technique, such as e.g., artificial neural networks (ANN) may be used.

(1) Constrained Non-Linear Programming (NLP) Using Predicted Elution Order as Constraint QSRR can be expressed as Formula 2 which is the formula of mathematical programming.

$$\min_a \sum_j (t_{R,j} - \hat{t}_{R,j})^2 \quad (2)$$

In Formula 2, $\hat{t}_{R,j}$=f(x) the modeled QSRR relation f(x) is a function with $a_i$ as a parameter. As in the embodiment to be described below, for example, when n=3 and when MLR is used as a relation model when=3, Formula 1 can be expressed as Formula 3.

$$\min_a \sum_j (t_{R,j} - \hat{t}_{R,j})^2 = \min_a \sum_j (t_{R,j} - a_1 x_{j,1} - a_2 x_{j,2} - a_3 x_{j,3})^2 \quad (3)$$

That is, a typical problem with QSRR is attributed to non-linear programming. By arranging the predicted retention times in ascending order, it is easy to predict the elution order therefrom. However, as described above, although it is possible to predict retention times of a number of peaks with adequate accuracy (i.e., within in a tolerable prediction error range) with the QSRR model obtained from Formula 2, prediction of elution order with the QSRR may often result in low accuracy. This is obvious when considered on the basis of the regression equation.

In terms of mathematical programming, the problems mentioned above seem to be solved by introducing the following inequality constraints:

$$\min_a \sum_j (t_{R,j} - a_1 x_{j,1} - a_2 x_{j,2} - a_3 x_{j,3})^2 \text{ subject to:} \quad (4)$$

$$\hat{t}_{R,j} \leq \hat{t}_{R,j+1} \text{ or}$$

$$a_1 x_{j,1} + a_2 x_{j,2} + a_3 x_{j,3} \leq a_1 x_{j+1,1} + a_2 x_{j+1,2} + a_3 x_{j+1,3}$$

For m compounds, the inequality constraints are represented as a vector-matrix notation $\bar{X} \cdot a \leq 0$, where $\bar{X}$ is a ((m−1)×3) matrix with [($x_{j,1}$−$x_{j+1,1}$) ($x_{j,2}$−$x_{j+1,2}$) ($x_{j,3}$−$x_{j+1,3}$)] as the j-th row (j=1, 2, ..., m−1), and a=[$a_1$ $a_2$ $a_3$]$^T$ is established.

However, some numerical experiments have shown that the above constraints are so excessive that even simple mixtures have bad results. As a result, a low retention time prediction error and an elution order prediction error are simultaneously obtained using the relaxed inequality constraints shown below.

$$\min_{\bar{a}} \left\{ \sum_{j=1}^{m} (t_{R,j} - a_1 x_{j,1} - a_2 x_{j,2} - a_3 x_{j,3})^2 + \sum_{j=1}^{m} \alpha_j \right\} \text{ subject to:} \quad (5)$$

$$a_1(x_{j,1} - x_{j+1,1}) + a_2(x_{j,2} - x_{j+1,2}) + a_3(x_{j,3} - x_{j+1,3}) - \alpha_j \leq 0$$

Where $\alpha_j$ is a positive relaxation parameter, $\bar{a}$ is a decision vector composed of a1, a2, a3 and $\alpha_j$ (j=1, 2, ..., m−1). The inequality constraints for m compounds can be expressed as a vector-matrix notation shown below.

$$\begin{bmatrix} x_{1,1}-x_{2,1} & x_{1,2}-x_{2,2} & x_{1,3}-x_{2,3} & -1 & 0 & 0 & \cdots & \cdots & 0 \\ x_{2,1}-x_{3,1} & x_{2,2}-x_{3,2} & x_{2,3}-x_{3,3} & 0 & -1 & 0 & \cdots & \cdots & 0 \\ \vdots & \vdots & \vdots & 0 & 0 & -1 & \cdots & \cdots & 0 \\ x_{j,1}-x_{j+1,1} & x_{j,2}-x_{j+1,2} & x_{j,3}-x_{j+1,3} & \vdots & \vdots & \vdots & \ddots & & \vdots \\ \vdots & \vdots & \vdots & \vdots & \vdots & \vdots & & \ddots & \vdots \\ x_{m-1,1}-x_{m,1} & x_{m-1,2}-x_{m,2} & x_{m-1,3}-x_{m,3} & 0 & 0 & 0 & \cdots & 0 & -1 \end{bmatrix} \begin{bmatrix} a_1 \\ a_2 \\ a_3 \\ \alpha_1 \\ \alpha_2 \\ \vdots \\ \alpha_j \\ \vdots \\ \alpha_{m-1} \end{bmatrix} \leq 0 \quad (6)$$

(2) Multi-Objective Optimization Using Retention Time Prediction Error and Elution Order Prediction Error as Objective Function (MOO)

The problem with multi-objective optimization (MOO) is attributed to optimization with multiple objective functions. The general formula thereof is Formula 7.

$$\min(g_1(\alpha_1), g_2(\alpha_2), \ldots, g_k(\alpha_k)) \quad (7)$$

subject to: $\alpha_i \in A$

In Formula 7, an integer k ($\geq$2) represents the number of objective functions g and a set A is a possible set of decision vectors $\alpha$. In a multi-objective optimization, normally there are no solutions that minimize all objective functions. Therefore, attention is paid to the Pareto optimal solution, which is a solution that cannot improve objective functions without degrading at least one of the objective functions.

In the present disclosure, two objective functions are used, one representing the error of the retention time prediction and the other representing the error of the elution order prediction. The Pareto optimal solution is then selected according to the following procedure: (1) selecting the knee point which is the best compromise between the retention time prediction error and the elution order prediction error from the Pareto front consisting of the Pareto solutions; (2) moving to the next Pareto solution to reduce the elution order prediction error; (3) validating the solution using the applicability domain; and (4) repeating (2) and (3) until an increase in the retention time prediction error reaches a first predetermined threshold or until an outlier in the applicability domain exceeds a second predetermined threshold. This is conceptually illustrated in FIG. 1.

Hereinafter, the present disclosure will be described in more detail with reference to Examples.

The examples presented herein are merely illustrative of the present disclosure and are not intended to limit the scope of the present disclosure.

Example

The following two examples demonstrate the applicability of the present disclosure: (i) CS1 which is a mixture of 62 organic compounds and (ii) CS2 which is a mixture of 98 synthetic peptides. Analysis for the first example CS1 was performed using a Supelcosil LC column with a gradient time of 10 minutes at 35° C. Analysis for the second example CS2 was performed using seven chromatographic columns (i.e., Xterra, Licrospher, PRP, Discovery RP-Amide C-16, Licrospher CN, Discovery HS F5-3 and Chromolith) at different gradient settings and temperatures. Chromatographic analysis data were obtained from the references.

The molecular descriptors used in each example for QSRR relation modeling are listed in Table 1 below.

TABLE 1

Molecular descriptors used in Examples (CS1 and CS2)

| Molecular descriptors | | Explanation |
|---|---|---|
| CS1 | $\mu$ | dipole moment |
| | $\delta_{min}$ | excess charge of the most negatively charged atom |
| | SASA | solvent-accessible surface area |
| CS2 | $Sum_{AA}$ | sum of retention times of respective 20 naturally occurring amino acids |
| | $vDW_{vol.}$ | Van der Waals volume |
| | clogP | computerized octanol-water coefficient |

In both examples, a linear model was considered as a specific form of the QSRR relation model, and control MLR model coefficients were calculated using a least-square method for comparison. The solution of a non-linear programming problem with relaxed constraints in Formula 5 was obtained using the interior-point method. The solution of a multi-objective optimization problem of Formula 7 was obtained using a genetic algorithm. In both methods, the coefficients of a control MLR model obtained for comparison were used as initial values in the optimization.

For the multi-objective optimization, the percentage root mean square error (%RMSE) of the retention time was used as an objective function representing a retention time prediction error.

$$\% \; RMSE(t_R) = \sqrt{\sum \left(\frac{t_R - \hat{t}_R}{t_R}\right)^2 / m} \times 100 \quad (8)$$

Where $t_R$ and $\hat{t}_R$ respectively represent the retention time measured through the analytical experiment and the retention time predicted by the model and m represents the number of mixtures measured for each column. The elution order prediction can be performed after sorting the retention times predicted by the QSRR model in ascending order, and %RMSE was used as the objective function representing the accuracy of the elution order.

$$\% \; RMSE \; (order) = \sqrt{\sum \left(\frac{order_{pred.} - order_{obs.}}{order_{obs.}}\right)^2 / m} \times 100 \quad (9)$$

Where $order_{obs.}$ and $order_{pred.}$ respectively represent the elution order determined through the analysis and the elution order determined from the predicted retention time.

Figure 2A:
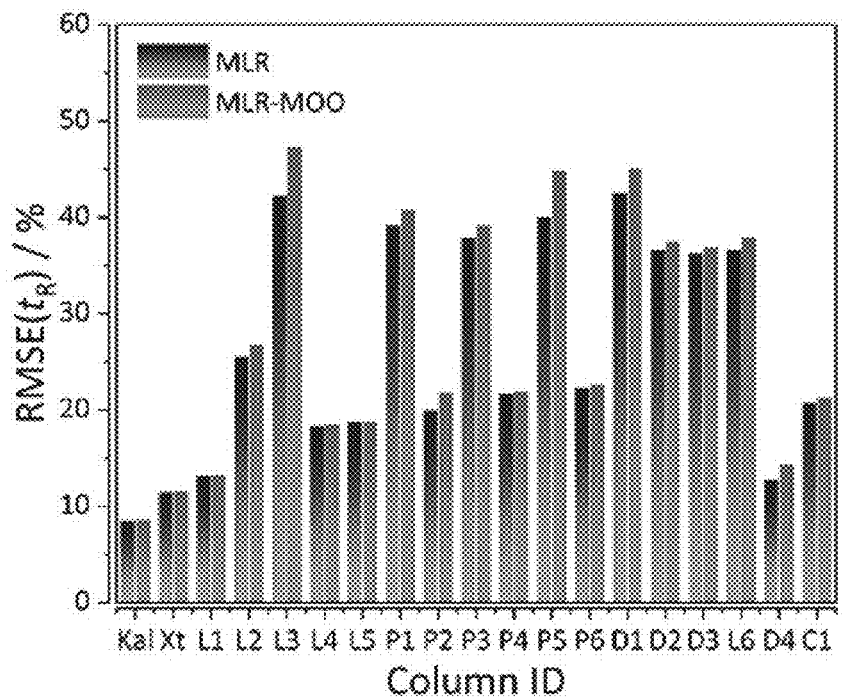
Figure 2B:
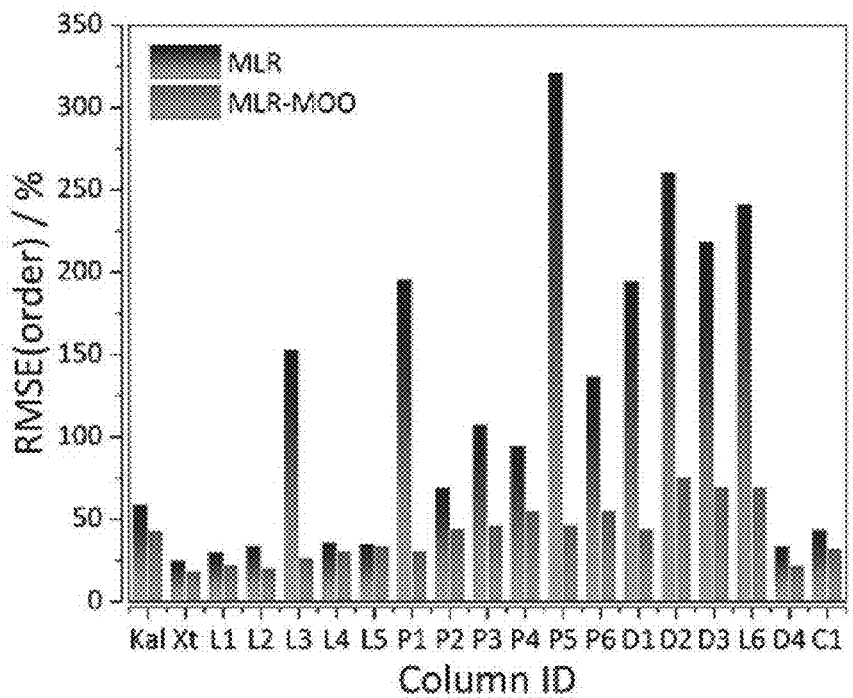
Figure 3A:
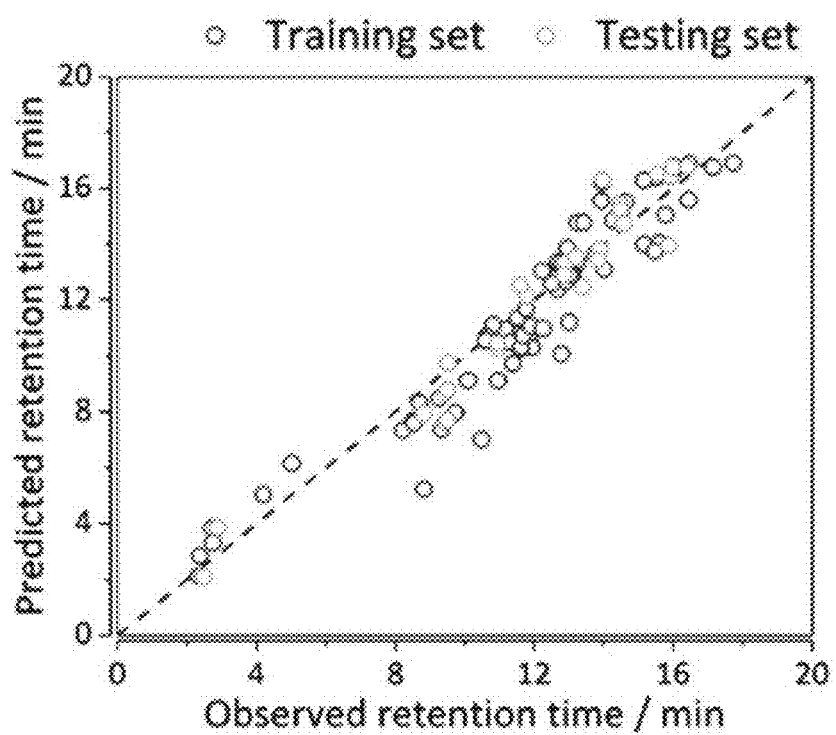
Figure 3B:
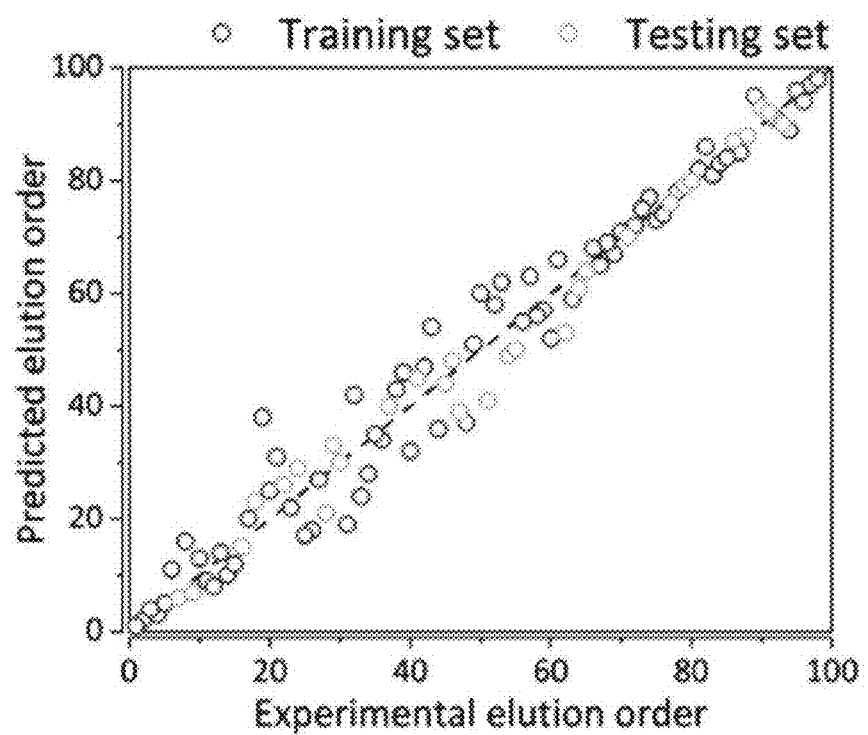
Figure 3C:
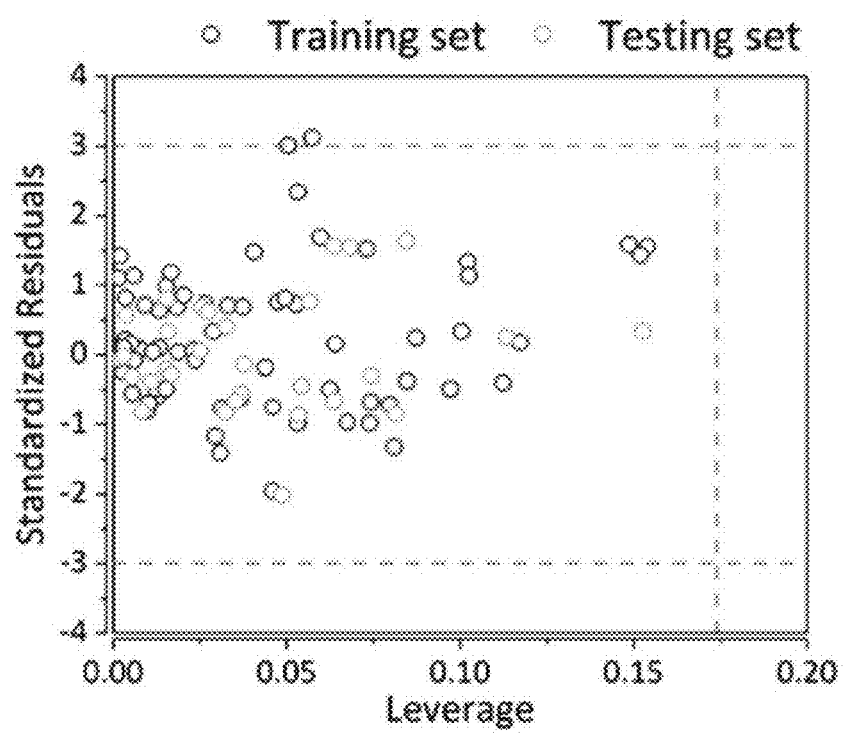
Figure 3D:
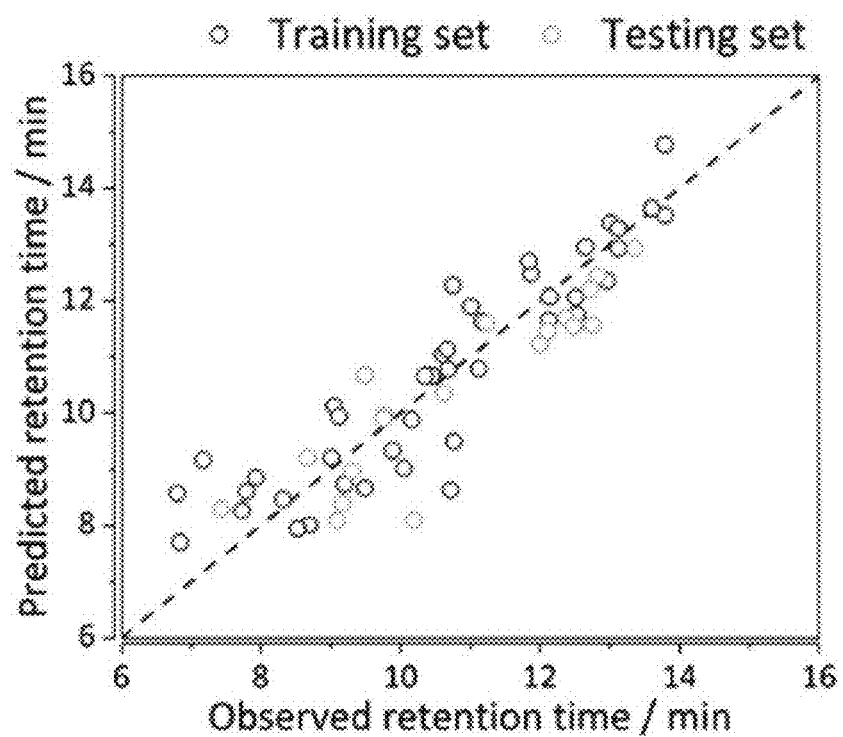
Figure 3E:
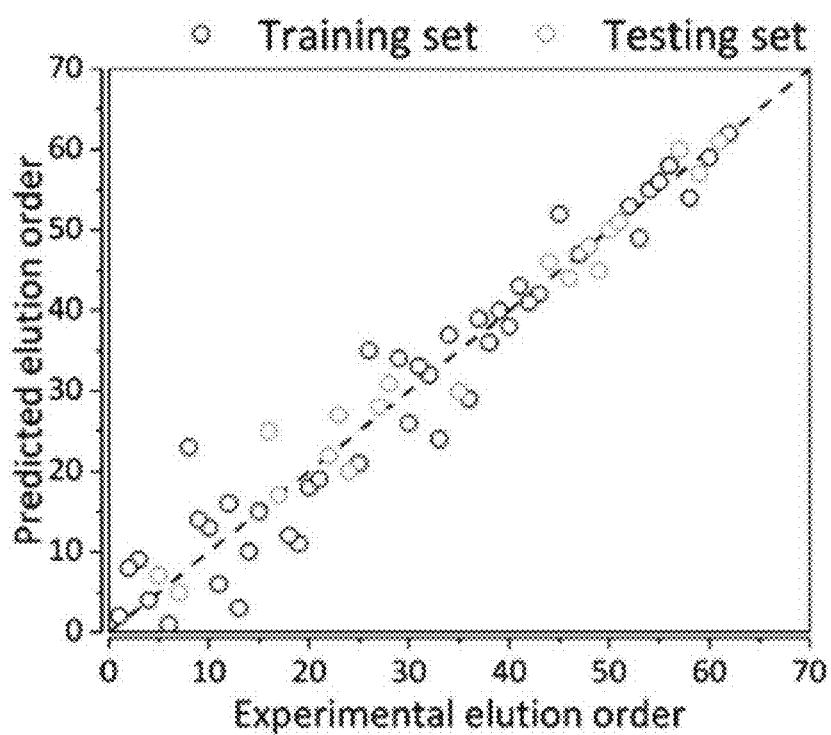
Figure 3F:
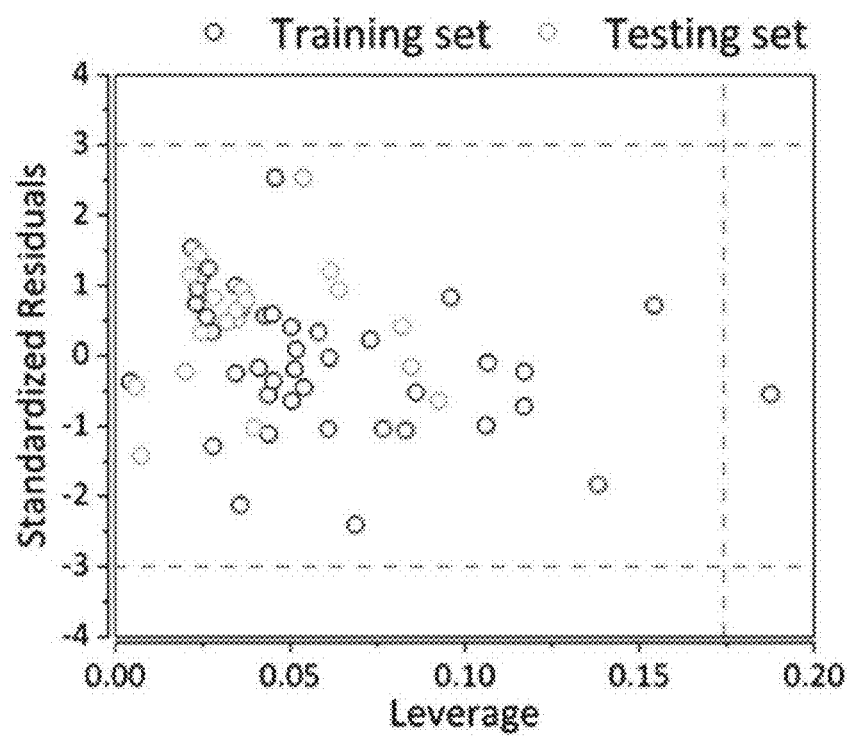
Figure 4A:
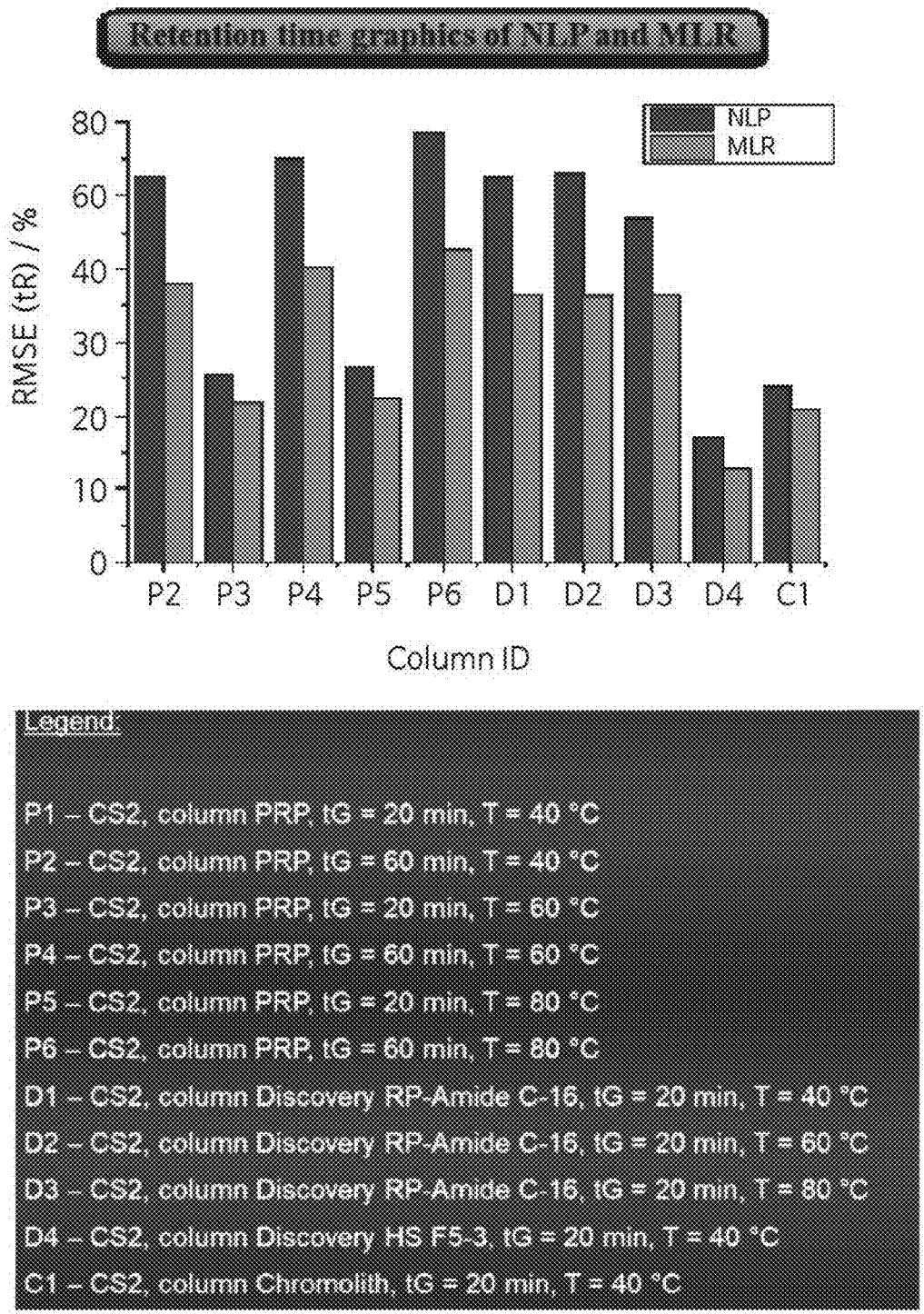
Figure 4B:
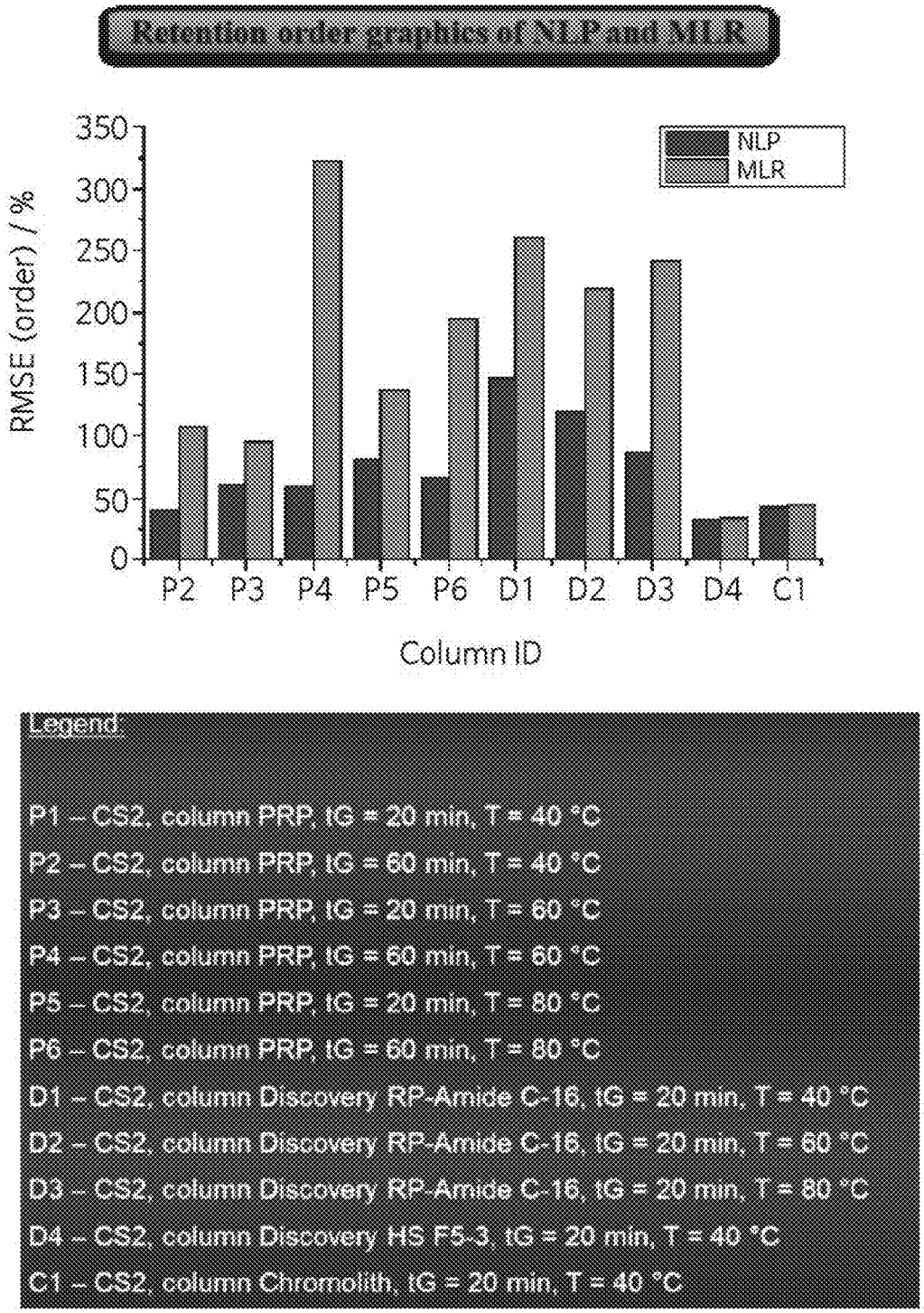
Figure 4C:
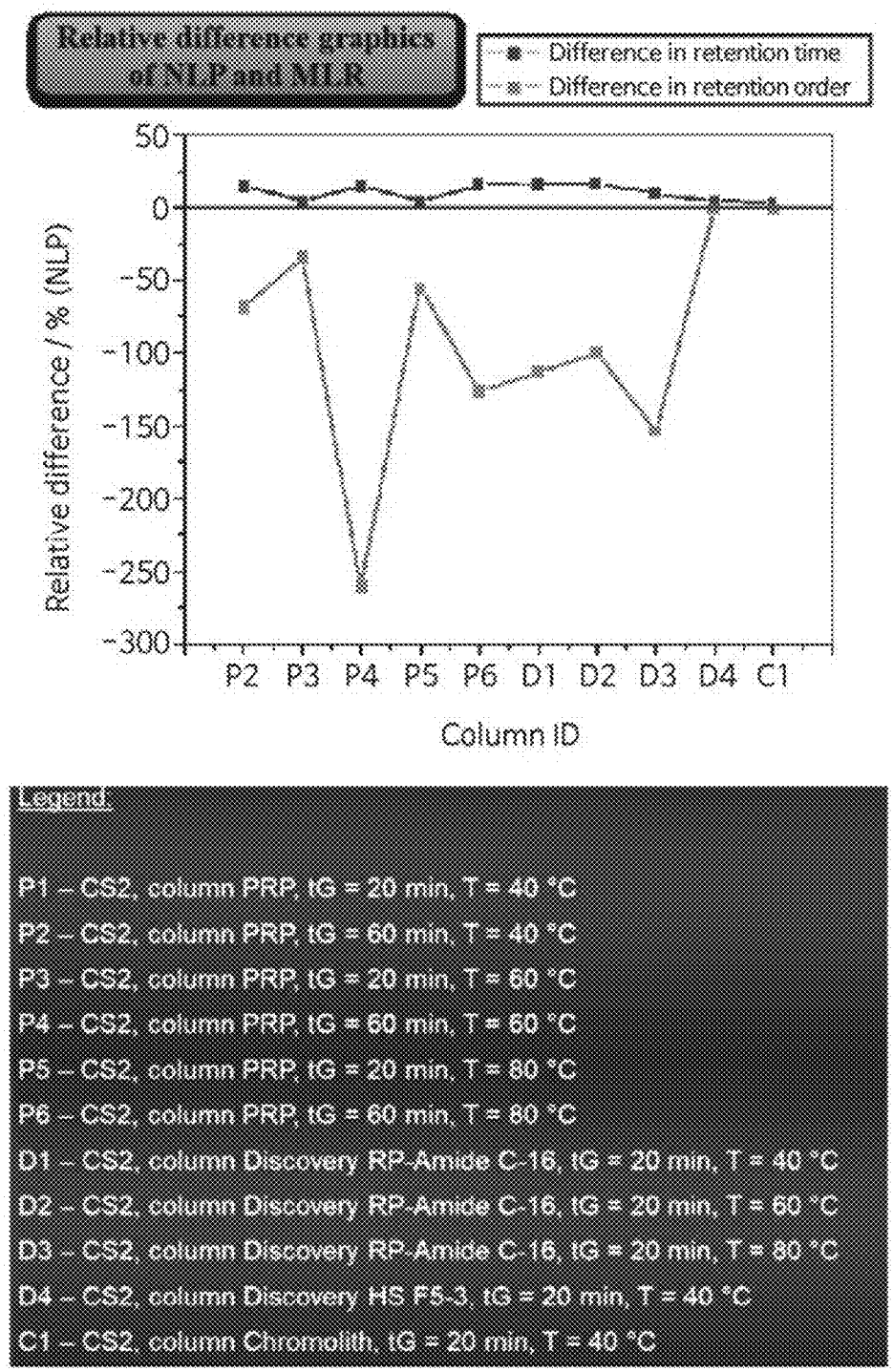

When both of the methods NLP and MOO used a linear QSRR model (MLR), the accuracy of the elution order prediction was significantly increased (see FIGS. 2B and 4B) at the expense of the accuracy of the retention time prediction in both examples (see FIGS. 2A and 4A). As illustrated in FIGS. 2C and 4C, the maximum increases in %RMSE (tR) were about 15% and 20%, respectively while the maximum decreases in %RMSE (order) were about 80% and 260%, respectively.

Figure 5A:
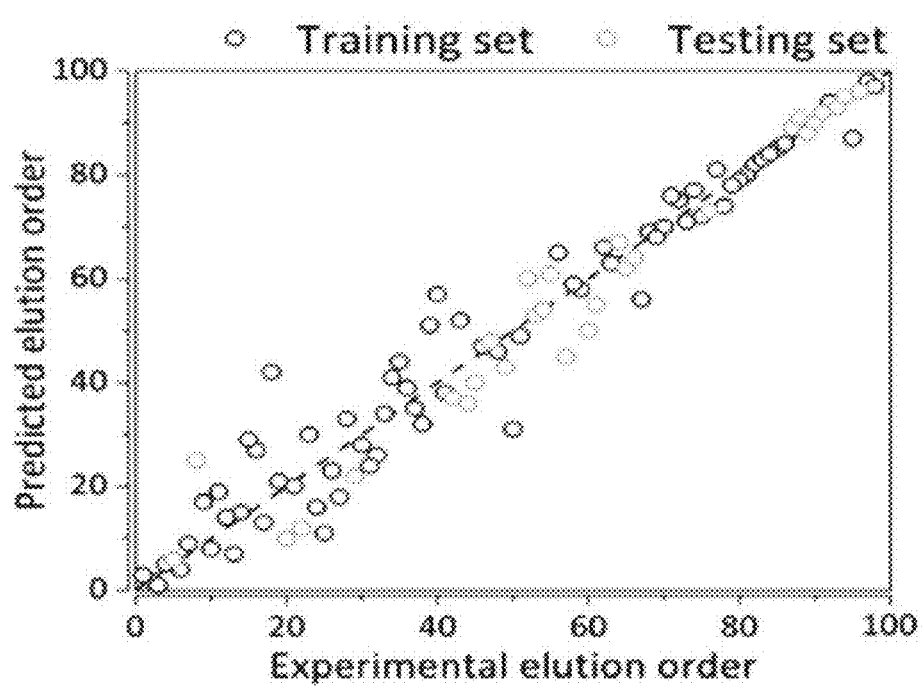
Figure 5B:
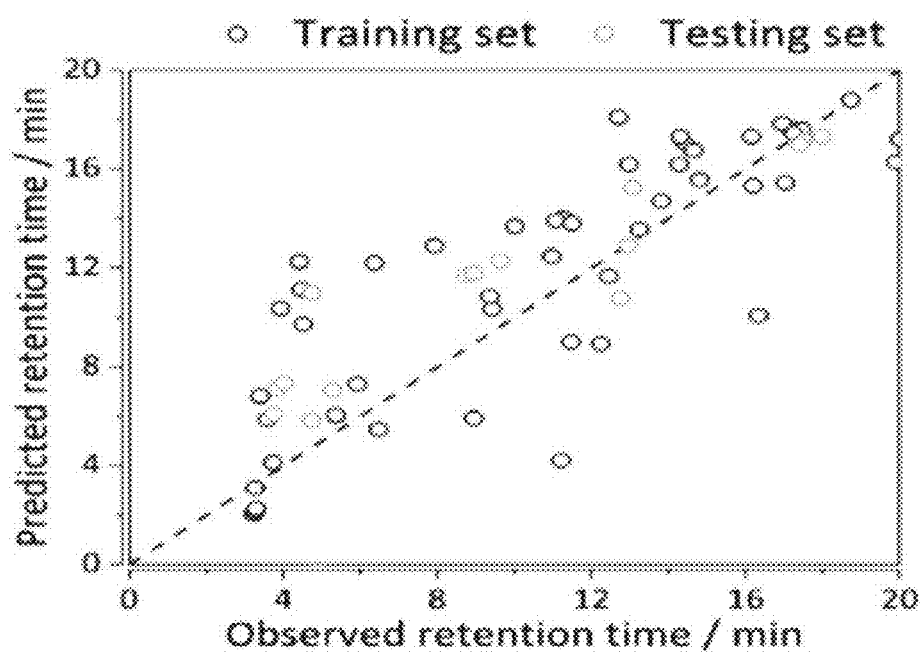
Figure 5C:
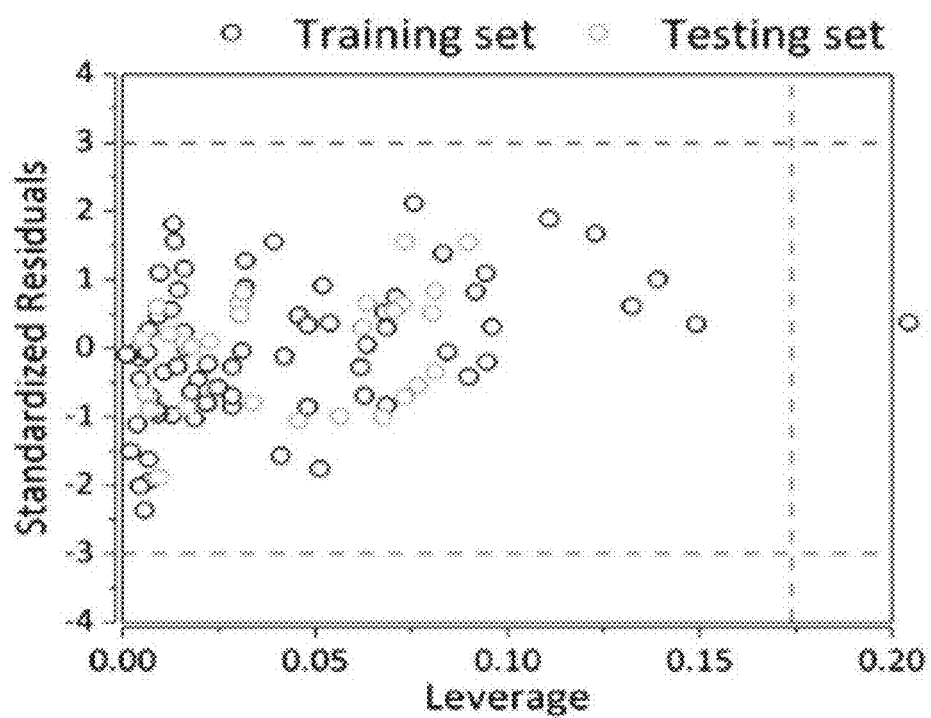

Of the seven RP-LC columns used for both methods in both examples, FIGS. 3 and 5 illustrate the prediction results for two columns in both examples (CS1: Supelcosil LC, tG=10 min, T=35° C.; CS2: Xterra, tG=20 min, T=40° C.). That is, the prediction performance for each of the retention time and the elution order and the corresponding applicability domain were shown. The two examples CS1 and CS2 (CS1 (FIGS. 3A and 3B); CS2 (FIGS. 3D, 3E, 5A, and 5B)) show reasonable retention time prediction performance and elution order prediction performance. Nearly all analyte compounds included in both examples were well predicted and structurally important analytes included in a training set were within each applicability domain (FIGS. 3C, 3F, and 5C). The developed model is therefore considered to be stable and robust for the structurally distant analytes.

Figure 6A:
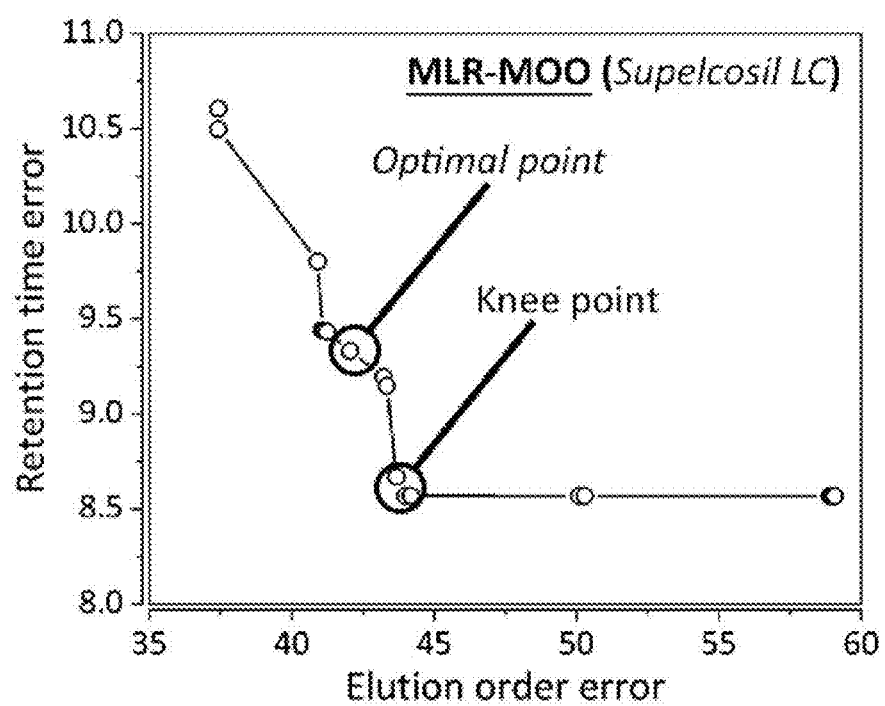
Figure 6B:
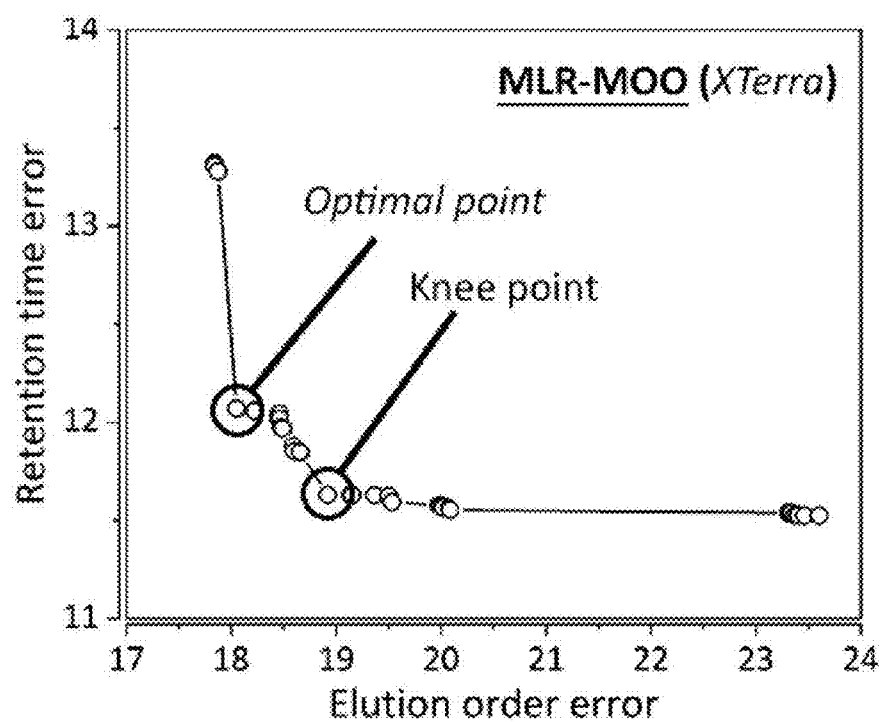

The optimal solutions obtained according to the procedure of finding the Pareto optimal solution while starting from the knee point are shown in FIG. 6A (CS1) and FIG. 6B (CS2). Predetermined thresholds were 10% (for %RMSE (tR)) at the knee point and 2 outliers in the applicability domain, respectively. In addition, as shown in Table 2 below, even in the case of the multi-objective optimization method, it was possible to attain a large decrease in elution order prediction error with a small increase in retention time prediction error in both of the examples.

TABLE 2

% RMSE at knee point and optimal point

| | | % RMSE($t_R$) | % RMSE(order) |
|---|---|---|---|
| CS1 | Knee point | 8.67 | 43.7 |
| | Optimal point | 9.33 | 42.0 |
| CS2 | Knee point | 11.6 | 19.8 |
| | Optimal point | 12.1 | 18.1 |

While exemplary embodiments of the present disclosure have been described with reference to the accompanying drawings, those skilled in the art will appreciate that the present disclosure can be implemented in other different forms without departing from the technical spirit or essential characteristics of the exemplary embodiments. Therefore, it is noted that the exemplary embodiments described above are only for illustrative purposes and are not restrictive in all aspects.

What is claimed is:

1. A computer-implemented method of predicting a chromatographic elution order of compounds in a mixture, the method comprising:
    generating, by a computer processor, a quantitative structure-retention relationship (QSRR) model;
    receiving, by the computer processor, mixture data representing one or more mixtures of a plurality of compounds;
    computer-modeling, by the computer processor, the QSRR model on the mixture data using artificial neural networks (ANN) to generate a non-linear programming (NLP) model comprising one or more inequality constraints;
    predicting, by the computer processor, a chromatographic elution order of the compounds in the mixture data using the NLP model, the predicting comprising obtaining a low retention time prediction error and an elution order prediction error, the one or more inequality constraints associated with the elution order prediction error;
    detecting, by the computer processor, positions of the compounds in the mixture data based on the predicted chromatographic elution order; and identifying, by the computer processor, one or more of the compounds based on the detected positions of the compounds, wherein the one or more inequality constraints comprise a positive relaxation parameter and a molecular descriptor associated with the elution order prediction error.

2. The method according to claim 1, wherein, in the predicting, the chromatographic elution order of the compounds in the mixture is predicted by the computer processor executing instructions comprising the non-linear programming (I) under the inequality constraints (II):

$$\min_{\bar{a}}\left\{\sum_{j=1}^{m}(t_{R,j} - a_1 x_{j,1} - a_2 x_{j,2} - a_3 x_{j,3})^2 + \sum_{j=1}^{m}\alpha_j\right\} \quad (I)$$

$$a_1(x_{j,1} - x_{j+1,1}) + a_2(x_{j,2} - x_{j+1,2}) + a_3(x_{j,3} - x_{j+1,3}) - \alpha_j \leq 0 \quad (II)$$

wherein the inequality constraints further comprise an $\bar{a}$ vector, and wherein:
- x represents the molecular descriptor,
- $t_R$ represents a retention time,
- m represents a number of the mixtures,
- j represents the positive relaxation parameter, and
- $\bar{a}$ represents the a vector comprising a1, a2, a3, and $a_j$ (j=1, 2, . . . , m–1).

3. The method according to claim 2, wherein the molecular descriptor comprises dipole moment (μ), excess charge of an atom that is most negatively charged ($\delta_{min}$), solvent-accessible surface area (SASA), sum of retention times of respective 20 naturally occurring amino acids ($Sum_{AA}$), Van der Waals volume ($vDW_{vol.}$), computerized octanol-water coefficient (c log P), or any combination thereof.

4. A computer-implemented method of predicting a chromatographic elution order of compounds in a mixture, the method comprising:
- generating, by a computer processor, a quantitative structure-retention relationship (QSRR) model, wherein the QSRR model comprises a molecular descriptor;
- receiving, by the computer processor, mixture data representing one or more mixtures of a plurality of compounds;
- computer-modeling, by the computer processor, the QSRR model on the mixture data to generate a linear model;
- predicting, by the computer processor, a chromatographic elution order of the compounds in the mixture data using the linear model by performing multi-objective optimization (MOO) on the basis of an objective function representing a retention time prediction error represented by Formula (III) and an elution order prediction error represented by Formula (IV):

$$\% \ RMSE(t_R) = \sqrt{\sum\left(\frac{t_R - \hat{t}_R}{t_R}\right)^2 / m} \times 100, \text{ and} \quad (III)$$

$$\% \ RMSE \text{ (order)} = \sqrt{\sum\left(\frac{order_{pred.} - order_{obs.}}{order_{obs.}}\right)^2 / m} \times 100; \quad (IV)$$

- detecting, by the computer processor, positions of the compounds in the mixture data based on the predicted chromatographic elution order; and
- identifying, by the computer processor, one or more of the compounds based on the detected positions of the compounds, wherein:
- $t_R$ and $\hat{t}_R$ respectively represent a retention time measured in an analytical experiment and a retention time predicted from the model,
- m represents a number of the mixtures measured for each column, and
- $order_{obs.}$ and $order_{pred.}$ respectively represent an elution order determined from the analytical experiment and an elution order determined from predicted retention times.

5. The method according to claim 4, wherein in the predicting, the MOO selects a Pareto optimal solution, selecting the Pareto optimal solution comprising:
- selecting a knee point which is an optimal compromise between the retention time prediction error and the elution order prediction error from a Pareto front including the Pareto solutions;
- moving to the next Pareto solution to reduce the elution order prediction error;
- verifying the solution using an applicability domain; and
- repeating the knee point selection and the moving until an increase in the retention time prediction error reaches a first predetermined threshold or an outlier in the applicability domain exceeds a second predetermined threshold.

6. The method of claim 4, wherein the linear model is represented by the following formula:

$$t_{R,j} = a_1 x_{j,1} + a_2 x_{j,2} + \ldots + a_n x_{j,n}$$

wherein:
- $t_{R,j}$ are retention times of respective compounds j sorted in ascending order,
- $x_{j,i}$ (i=1, . . . , n) are the molecular descriptors of respective compounds j, and
- $a_i$ (i=1, . . . , n) are regression coefficients.

7. The method according to claim 6, wherein the molecular descriptor comprises dipole moment (μ), excess charge of an atom that is most negatively charged ($\delta_{min}$), solvent-accessible surface area (SASA), sum of retention times of respective 20 naturally occurring amino acids ($Sum_{AA}$), Van der Waals volume ($vDW_{vol.}$), computerized octanol-water coefficient (c log P), or any combination thereof.

* * * * *